(12) United States Patent
Schraga

(10) Patent No.: US 6,958,072 B2
(45) Date of Patent: Oct. 25, 2005

(54) SINGLE USE LANCET DEVICE

(76) Inventor: Steven Schraga, 9433 Byron Ave., Surfside, FL (US) 33154

(*) Notice: Subject to any disclaimer, the term of this patent is extended or adjusted under 35 U.S.C. 154(b) by 204 days.

(21) Appl. No.: 10/171,464

(22) Filed: Jun. 13, 2002

(65) Prior Publication Data

US 2003/0050656 A1 Mar. 13, 2003

Related U.S. Application Data

(63) Continuation-in-part of application No. 09/709,738, filed on Nov. 10, 2000, now Pat. No. 6,514,270

(60) Provisional application No. 60/297,826, filed on Jun. 13, 2001.

(51) Int. Cl.$^7$ ............................................. A61B 17/14
(52) U.S. Cl. ..................... 606/182; 606/181; 606/184; 606/185
(58) Field of Search ............................... 606/181, 182, 606/184, 185

(56) References Cited

U.S. PATENT DOCUMENTS

| | | |
|---|---|---|
| 2,711,738 A | 6/1955 | Kelly et al. |
| 3,483,810 A | 12/1969 | Peters et al. |
| 3,906,626 A | 9/1975 | Riuti |
| 4,373,526 A | 2/1983 | Kling |
| 4,469,110 A | 9/1984 | Slama |
| 4,573,976 A | 3/1986 | Sampson et al. |
| 4,610,620 A | 9/1986 | Gray |
| 4,655,750 A | 4/1987 | Vaillancourt |
| 4,735,202 A | 4/1988 | Williams |
| 4,752,290 A | 6/1988 | Schramm |
| 4,758,231 A | 7/1988 | Haber et al. |
| 4,863,436 A | 9/1989 | Glick |
| 4,895,147 A | 1/1990 | Bodicky et al. |
| 4,897,083 A | 1/1990 | Martell |
| 4,908,023 A | 3/1990 | Yuen |
| 4,944,736 A | 7/1990 | Holtz |
| 4,994,045 A | 2/1991 | Ranford |
| 4,994,068 A | 2/1991 | Hufnagle |
| 5,024,660 A | 6/1991 | McNaughton |
| 5,026,388 A | 6/1991 | Ingalz |
| 5,057,079 A | 10/1991 | Tiemann et al. |
| 5,088,996 A | 2/1992 | Kopfer et al. |
| 5,116,351 A | 5/1992 | Frassetti |

(Continued)

FOREIGN PATENT DOCUMENTS

| | | |
|---|---|---|
| EP | 0 668 049 A1 | 8/1995 |
| EP | 0 894 471 A2 | 2/1999 |
| WO | WO 91/00215 | 1/1991 |
| WO | WO 00/78203 A2 | 12/2000 |

Primary Examiner—Glenn K. Dawson
Assistant Examiner—Darwin P. Erezo
(74) Attorney, Agent, or Firm—Malloy & Malloy, P.A.

(57) ABSTRACT

A single use lancet device having a housing, a lancet with a piercing tip movably disposed in the housing and structured to move between a cocked orientation and a piercing orientation, and a driving assembly structured to move the lancet into the piercing orientation. A retention member and an engagement hub are further provided and structured to be cooperatively engaged with one another upon the lancet being disposed in the cocked orientation so as to maintain the lancet in the cocked orientation until released by an actuation assembly. Specifically, the actuation assembly is structured to move between an actuated and an un-actuated orientation, movement into the actuated orientation releasing the retention member and the engagement hub from their cooperative engagement with one another and thereby result in movement of the lancet into the piercing orientation. The device also includes a restrictor assembly structured to substantially prevent the actuation assembly from moving out of the actuated orientation, thereby preventing re-firing of the lancet utilizing the actuation assembly.

25 Claims, 4 Drawing Sheets

U.S. PATENT DOCUMENTS

| | | |
|---|---|---|
| 5,147,326 A | 9/1992 | Talonn et al. |
| 5,147,375 A * | 9/1992 | Sullivan et al. .............. 606/182 |
| 5,160,326 A | 11/1992 | Talonn et al. |
| 5,181,609 A | 1/1993 | Spielmann et al. |
| 5,207,696 A | 5/1993 | Matwijcow |
| 5,219,333 A | 6/1993 | Sagstetter et al. |
| 5,222,945 A | 6/1993 | Basnight |
| 5,224,950 A | 7/1993 | Prywes |
| 5,241,969 A | 9/1993 | Carson et al. |
| 5,247,972 A | 9/1993 | Tetreault |
| 5,250,026 A | 10/1993 | Ehrlich et al. |
| 5,250,063 A | 10/1993 | Abidin et al. |
| 5,279,581 A | 1/1994 | Firth et al. |
| 5,297,599 A | 3/1994 | Bucheli |
| 5,304,136 A | 4/1994 | Erskine et al. |
| 5,304,192 A | 4/1994 | Crouse |
| 5,312,347 A | 5/1994 | Osborne et al. |
| 5,312,365 A | 5/1994 | Firth et al. |
| 5,318,583 A | 6/1994 | Rabenau et al. |
| 5,318,584 A | 6/1994 | Lange et al. |
| 5,330,492 A | 7/1994 | Haugen |
| 5,336,199 A | 8/1994 | Castillo et al. |
| 5,346,480 A | 9/1994 | Hess et al. |
| 5,350,392 A | 9/1994 | Purcell et al. |
| 5,356,406 A | 10/1994 | Schraga |
| 5,356,420 A | 10/1994 | Czernecki et al. |
| 5,361,902 A | 11/1994 | Abidin et al. |
| 5,395,388 A | 3/1995 | Schraga |
| 5,417,662 A | 5/1995 | Hjertman et al. |
| 5,423,847 A | 6/1995 | Strong et al. |
| 5,439,473 A | 8/1995 | Jorgensen |
| 5,454,828 A | 10/1995 | Schraga |
| 5,462,535 A | 10/1995 | Bonnichsen et al. |
| 5,464,418 A | 11/1995 | Schraga |
| 5,468,233 A | 11/1995 | Schraga |
| 5,469,964 A | 11/1995 | Bailey |
| 5,487,748 A | 1/1996 | Marshall et al. |
| 5,496,340 A | 3/1996 | Abidin et al. |
| 5,501,672 A | 3/1996 | Firth et al. |
| 5,518,004 A | 5/1996 | Schraga |
| 5,527,334 A | 6/1996 | Kanner et al. |
| 5,531,713 A | 7/1996 | Mastronardi et al. |
| D376,203 S | 12/1996 | Schraga |
| 5,584,846 A | 12/1996 | Mawhirt et al. |
| 5,599,323 A | 2/1997 | Bonnichsen et al. |
| 5,628,764 A * | 5/1997 | Schraga ..................... 606/182 |
| 5,643,306 A | 7/1997 | Schraga |
| 5,697,916 A | 12/1997 | Schraga |
| 5,706,942 A | 1/1998 | Vila et al. |
| 5,707,384 A | 1/1998 | Kim |
| 5,730,753 A | 3/1998 | Morita |
| 5,735,823 A | 4/1998 | Berger |
| 5,738,665 A | 4/1998 | Caizza et al. |
| 5,741,288 A | 4/1998 | Rife |
| 5,746,761 A | 5/1998 | Turchin |
| 5,755,733 A | 5/1998 | Morita |
| 5,772,636 A | 6/1998 | Brimhall et al. |
| 5,792,122 A | 8/1998 | Brimhall et al. |
| 5,797,940 A | 8/1998 | Mawhirt et al. |
| 5,797,942 A | 8/1998 | Schraga |
| 5,836,920 A | 11/1998 | Robertson |
| 5,868,771 A | 2/1999 | Herbert et al. |
| 5,873,856 A | 2/1999 | Hjertman et al. |
| 5,891,103 A | 4/1999 | Burns |
| 5,908,434 A | 6/1999 | Schraga |
| 5,947,934 A | 9/1999 | Hansen et al. |
| 5,951,530 A | 9/1999 | Steengaard et al. |
| 5,951,582 A | 9/1999 | Thorne et al. |
| 5,954,738 A | 9/1999 | LeVaughn et al. |
| 5,968,021 A | 10/1999 | Ejlersen |
| 5,971,966 A | 10/1999 | Lav |
| 5,980,491 A | 11/1999 | Hansen |
| 5,984,906 A | 11/1999 | Bonnichsen et al. |
| 6,015,397 A | 1/2000 | Elson et al. |
| 6,022,366 A | 2/2000 | Schraga |
| 6,050,977 A | 4/2000 | Adams |
| 6,056,765 A | 5/2000 | Bajaj et al. |
| 6,074,372 A | 6/2000 | Hansen |
| 6,077,253 A | 6/2000 | Cosme |
| 6,106,537 A * | 8/2000 | Crossman et al. .......... 606/181 |
| 6,110,149 A | 8/2000 | Klitgaard et al. |
| 6,149,608 A | 11/2000 | Marshall et al. |
| 6,156,051 A | 12/2000 | Schraga |
| 6,168,606 B1 | 1/2001 | Levin et al. |
| 6,190,398 B1 | 2/2001 | Schraga |
| 6,213,977 B1 | 4/2001 | Hjertman et al. |
| 6,216,868 B1 | 4/2001 | Rastegar et al. |
| 6,228,100 B1 | 5/2001 | Schraga |
| 6,258,112 B1 | 7/2001 | Schraga |
| 6,302,869 B1 | 10/2001 | Klitgaard |
| 6,322,574 B1 | 11/2001 | Lloyd et al. |
| 6,322,575 B1 | 11/2001 | Schraga |
| 6,346,114 B1 | 2/2002 | Schraga |
| 6,358,265 B1 | 3/2002 | Thorne, Jr. et al. |
| 6,514,270 B1 | 2/2003 | Schraga |
| 6,530,937 B1 | 3/2003 | Schraga |

* cited by examiner

SINGLE USE LANCET DEVICE

CLAIM OF PRIORITY

The present application is a Continuation-In-Part patent application of previously filed, now patent application having Ser. No. 60/297,826, filed on Jun. 13, 2001, which is a Continuation-In-Part of U.S. patent application having Ser. No. 09/709,738 filed Nov. 10, 2000 now U.S. Pat. No. 6,514,270, also incorporated herein in its entirety by reference.

BACKGROUND OF THE INVENTION

1. Field of the Invention

The present invention relates to a single use lancet device structured to be conveniently and effectively utilized for various blood sampling procedure, but which is also substantially safe, preventing re-firing of the device after it has been used, and thereby preventing and/or substantially minimizing inadvertent contamination of a patient and/or other personnel as a result of a used and potentially contaminated lancet. Furthermore, the device is compact and easy to utilize in a cost effective and preferably fully disposable manner.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety are typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to ensure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize, affirmatively preventing re-use, once contaminated. Additionally, it is noted that while other devices may be provided to prevent the lancet form even being cocked, it would still be beneficial to provide a device that even if the lancet is re-cocked does not allow for additional and/or secondary firing.

SUMMARY OF THE INVENTION

The present invention is directed to a single use lancet device of the type commonly utilized for various blood sampling purposes. In particular, the single use lancet device of the present invention includes a housing and a lancet. The lancet, which also includes a piercing tip, is movably disposed in the housing and is structured to move at least between a cocked orientation and a piercing orientation. A driving assembly is provided so as to actually move the lancet at least temporarily into the piercing orientation.

The lancet may be retained in the cocked orientation by means of at least one embodiment of a retention assembly. In this embodiment of the present invention, at least one retention member and a corresponding engagement hub are cooperatively disposed. In particular, the engagement hub is structured to be cooperatively engaged with the retention member, at least when the lancet is disposed in the cocked orientation. As a result, the retention member and the engagement hub, which may be cooperatively engaged with the housing and the lancet, effectively maintain the lancet in the cocked orientation until they are released from that engagement with one another. As such, it is seen, in this embodiment, that when the lancet is ready for use, it is maintained in the cocked, ready to fire orientation until that time.

In order to release the lancet, and more particularly the cooperative engagement between the retention member and the engagement hub of the illustrated embodiment, the present invention further includes an actuation assembly. Specifically the actuation assembly is structured to move between an actuated and an un-actuated orientation. In this regard, movement of the actuation assembly into the actuated orientation is structured to release at least the retention member and the engagement hub from their cooperative engagement with one another, thereby resulting in movement of the lancet into the piercing orientation.

In order to substantially minimize the inadvertent re-use of the single use lancet device of the present invention, a restriction assembly is also preferably provided. Specifically, the restriction assembly is structured to substantially prevent the actuation assembly from moving from a piercing orientation towards a cocked orientation and out of the aforementioned actuated orientation. In this regard, the restriction assembly may include a stop member preferably in the form of at least one abutment structure that is fixedly mounted on the housing. In addition, the restriction assembly includes a restrictor member mounted at least on the lancet member and in abutting relation with the stop member as the restrictor member travels in the direction of the cocked orientation from the piercing orientation. As such, once the lancet device of the present invention has been fired the actuation assembly and/or lancet cannot move back into its un-actuated orientation/cocked orientation for a subsequent firing, regardless of whether the lancet itself may or may not be moved back into the cocked orientation.

These and other features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Looking to the Figures, the present invention is directed to a single use lancet device, generally indicated as 10. In particular, the single use lancet device 10 is structured to be utilized so as to pierce a patient's skin, such as with the piercing tip 25 of a lancet 24 in order to obtain a blood specimen from the patient. Furthermore, the present single use lancet device 10 is preferably configured to be substantially small and compact, and structured so as to permit only a single use thereof. The spread of disease and/or other contaminants from the inadvertent and/or deliberate reuse of such a single use lancet device 10 will thereby be prevented.

The single use lancet device 10 of the present invention preferably includes a housing 20. The housing 20 is preferably generally rigid and compact so as to be easily and comfortably held and manipulated by the user. In this regard, the housing 20 may be contoured and/or have any configuration that can be effectively and conveniently held and operated by a user. Movably contained within the housing is a lancet 24. In particular, the lancet 24 preferably includes a piercing tip 25 that extends outwardly from a front or leading end 24' of a movable body 24", which is to be considered a part of the lancet 24. Further, the lancet 24 is structured to be contained within an interior of the housing 20 and to move therein, as will be described in greater detail hereinafter.

Figure 5:
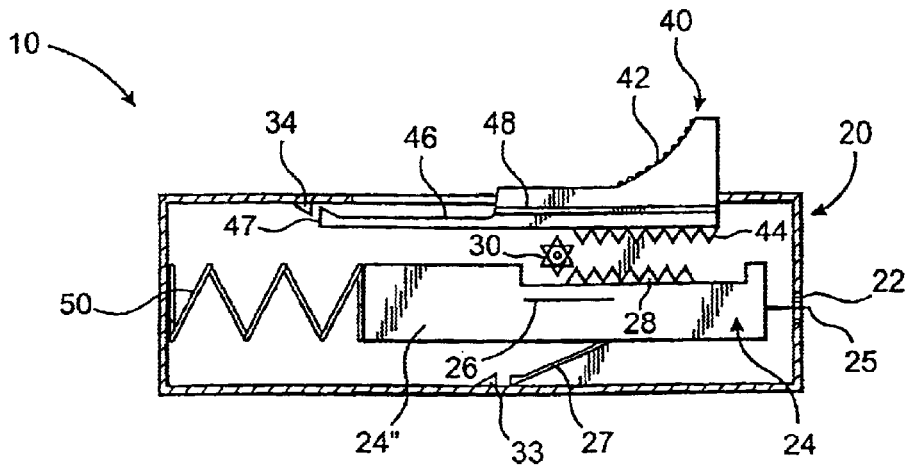
FIG. 5 is a side view of the embodiment of FIG. 2 illustrating the lancet disposed in a piercing orientation and the actuation assembly in a locked orientation.
Figure 6:
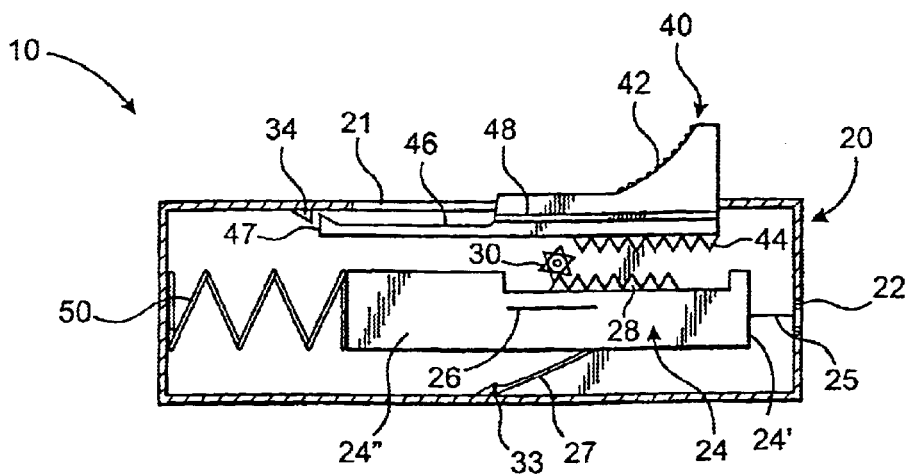
FIG. 6 is a side view of the embodiment of FIG. 2 illustrating a retracted orientation after the firing of single use lancet device of the present invention.

A driving assembly, preferably in the form of a biasing element 50, is disposed and/or connected relative to the lancet 24 so as to force it into a piercing orientation, best illustrated in FIG. 5. Furthermore, the lancet 24 preferably only temporarily achieves the piercing orientation illustrated in FIG. 5, after which it is retracted into an interior of the housing 20, as illustrated in FIG. 6. Once retracted, the piercing tip 25 is disposed within the housing 20 and is thereby effectively concealed and prevented from inadvertent contact with the user, patient, etc. Moreover, as will also be described hereinafter, in the retracted orientation of FIG. 6, one or more structural components are preferably incorporated in the single use lancet device 10 that prevent the lancet 24 from being effectively re-fired.

Figure 1:
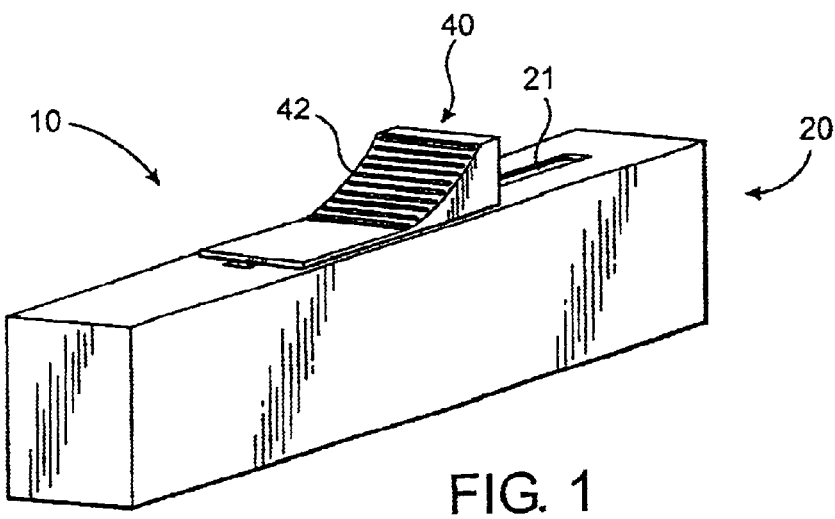
FIG. 1 is a rear perspective illustration of an embodiment of the single use lancet device of the present invention.
Figure 2:
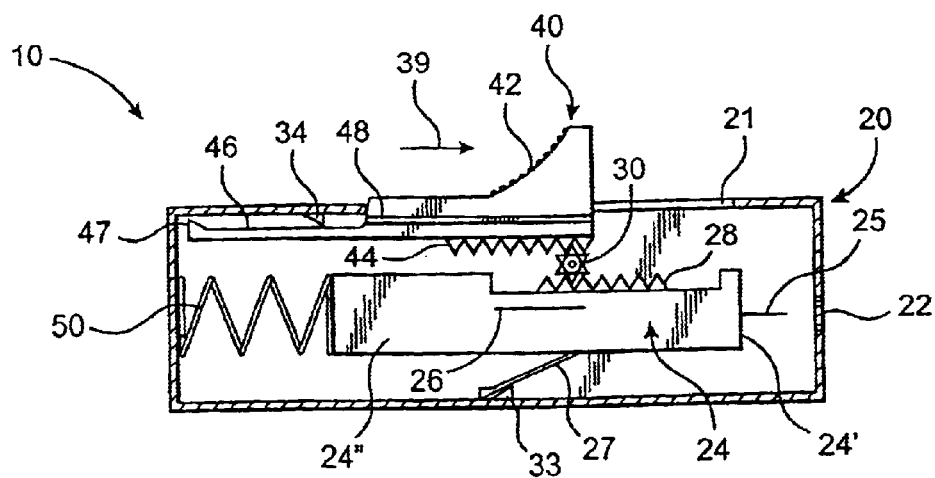
FIG. 2 is an interior longitudinal cross sectional view of an embodiment of the single use lancet device of the present invention in an un-cocked, un-fired orientation.
Figure 3:
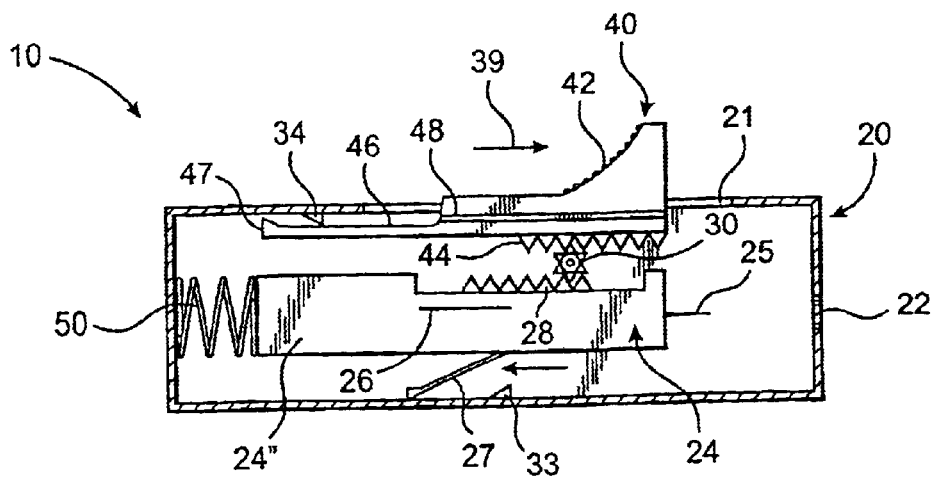
FIG. 3 is an illustration of the embodiment of FIG. 2 wherein the lancet is disposed under tension and in a ready to fire orientation.
Figure 4:
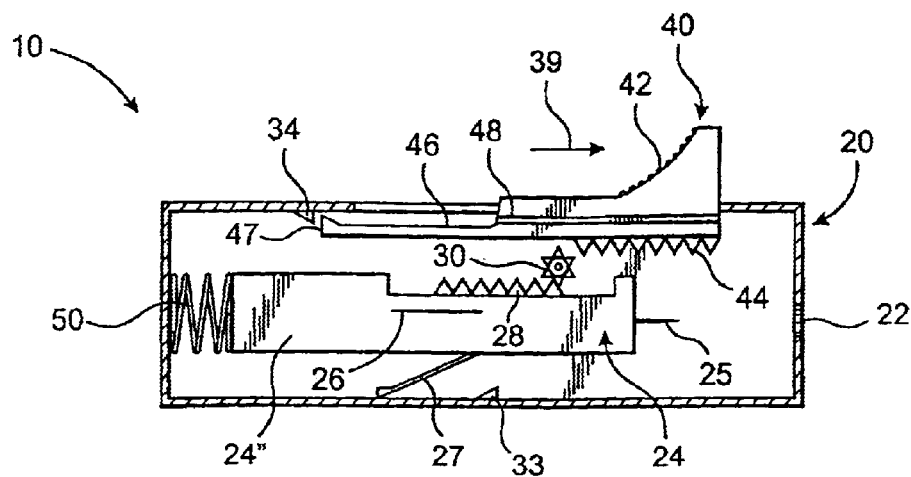
FIG. 4 is side view of the embodiment of FIG. 2 illustrating a release point between the lancet and the actuation assembly so as to permit the lancet to be fired.

In order to achieve movement of the lancet 24 into a generally cocked, under tension orientation, the single use lancet device 10 also preferably includes an actuation assembly 40. In addition, the lancet 24 preferably moves within the housing 20 while being maintained in a properly aligned orientation by one or more guide tracks or wings 26. Further, various embodiments of the present invention include a positioning assembly which comprises at least one positioning member. The positioning member may be in the form of a gear member 30 movably and detachably connected between the actuation assembly 40 and the lancet 24. In particular, the positioning assembly is configured so as to move the lancet 24 rearward, compressing the biasing element 50 and placing the lancet 24 under tension, when the actuation assembly 40 is pushed forward as indicated by directional arrow 39, such as by a thumb of the user. As a result, when an unfired lancet 24, as illustrated in FIG. 2, is grasped, the user merely pushes forward on the actuation assembly 40. The actuation assembly 40 at least partially extends into the interior of the housing 20, such as by passing through an actuation access opening 21. When moved forward, the lancet 24 is caused to move rearward toward or into the cocked orientation by virtue of the at least one positioning member such as gear 30.

Eventually, the actuation assembly 40 will be pushed forward to a sufficient degree to achieve a release point where the positioning member or gear 30 will be released or detached from concurrent inter connection with both the lancet 24 and the actuation assembly 40, as will be described hereinafter. Upon the actuation assembly reaching the release point, the tension exerted on the lancet 24 by the biasing element 50 causes the lancet 24 to be driven forward temporarily into its piercing orientation, as illustrated in FIG. 5. Subsequently, as disclosed in FIG. 6, the biasing element 50 will return automatically to its normally relaxed position, thereby forcing the lancet 24, and in particular the piercing tip 25, back into the housing 20 into a retracted orientation disclosed in FIG. 6. In its retracted orientation, the piercing tip 25 will be contained within the housing 20 thereby preventing inadvertent contact or engagement of the piercing tip 20 with any person or object.

Looking to the embodiment of FIGS. 1 through 6, the actuation assembly 40 includes an exterior portion 42 which is structured to be manipulated by a user, such as by engagement with the user's thumb. As such, the actuation assembly 40 preferably slides relative to the housing 20 in a generally parallel orientation to the movement of the lancet 24, preferably through the provision of a guide track or wing 48. Exposed, preferably on an underside of the actuation assembly 40, however, is a track element 44.

More specifically, the track element 44 is structured to operatively engage the rotating gear 30 of the positioning assembly. The gear 30 is connected to the housing 20, but freely rotates therein. Moreover, the lancet 24 preferably also includes a corresponding track 28 which also engages the interconnecting, rotating gear 30. Accordingly, as the track 44 on the actuation assembly 40 moves forward, the gear 30 rotates clockwise and because of its engagement with the track 28, causes the lancet 24 to be pulled or moved rearward within the housing 20. The track 44 on the actuation assembly 40, however, has only a predetermined limited length, and as such, when a clearance point is reached, as in FIG. 4, the track 44 no longer engages the gear 30. The gear 30 can then freely rotate allowing the lancet 24 to be urged forward into the piercing orientation as a result of the force exerted thereon by the biasing element 50. In this regard, one fluid, forward pushing movement of the actuation assembly 40 achieves a movement of the lancet 24 first into the cocked orientation and then into the piercing orientation. In the piercing orientation the piercing tip 25 engages a patient as intended.

In order to prevent the single use lancet device 10 of the present invention from being re-used, one or more safety structures have been provided. In particular, a restriction assembly is preferably provided and cooperatively disposed between the lancet 24 and the housing 20. In the embodiment of FIG. 2, the restriction assembly comprises a restrictor member, which may take the form of a biasing element 27 protruding from the movable body 24" of the lancet 24. When moving in a forward direction (see directional arrow 39), the biasing element 27 is structured to freely pass over a stop member or abutment 33 preferably fixedly disposed on the interior of the housing 20. As the lancet 24 is forced into its piercing orientation, the biasing element 27 does not restrictively engage abutment 33. However, as the lancet 24 is retracted in a rearward direction, back into the interior of the housing 20, the biasing element 27 and the stop member or abutment 33 are relatively disposed and cooperatively structured to restrictively engage one another and limit the rearward movement of the lancet 24. As a result, the lancet 24 can not be pushed rearward into a generally cocked orientation and therefore can not be re-fired.

As an additional safety measure, however, the actuation assembly 40 is preferably configured such that it may fire the single use lancet device 10 only a single time. Looking to the embodiment of FIG. 2, the actuation assembly 40 may include a trailing portion 46 within an abutment head 47. In particular, the abutment head 47 is preferably generally angled, or otherwise configured, to move freely over a corresponding abutment element 34 in the housing 20 when the actuation assembly 40 is moved forward (see directional arrow 39) during firing of the lancet 24. Accordingly, when the actuation assembly 40 has moved forward sufficiently so as to release or be disconnected from the gear 30, the lancet 24 will be forced forward, into the piercing orientation. The abutment head 47 will then have passed over the cooperatively structured stop or abutment element 34. Subsequent to the firing of the lancet 24, restrictive engagement between the abutment element 34 and the abutment head 47 will limit rearward movement of the actuation assembly 40 to a point where it cannot re-engage the gear 30 of the positioning assembly. Re-firing of the single use lancet device 10 is thereby further prevented.

Figure 7:
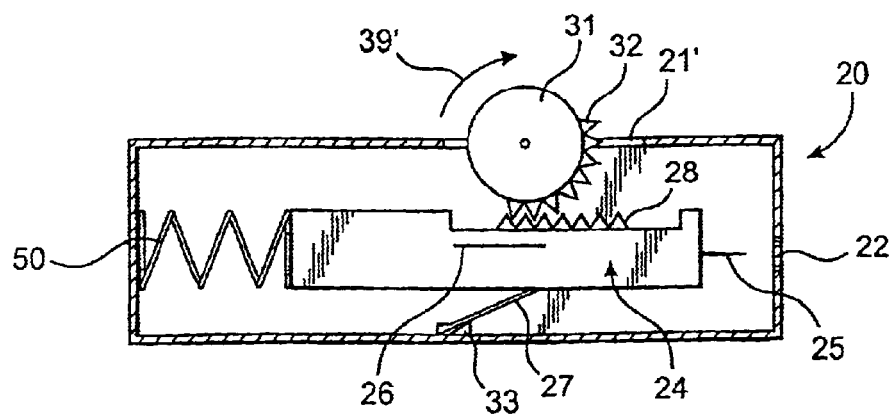
FIG. 7 is a side cross sectional view of an alternative embodiment of the single use lancet device of the present invention.

Looking to the embodiment of FIG. 7, the actuation assembly differs from the embodiment of FIGS. 1 through 6 and comprises a rotationally mounted actuation member 31 that protrudes outwardly from housing 20 through an access opening 21'. In this embodiment, the positioning member of the positioning assembly comprises a gear segment 32 formed along a portion of the periphery of actuation member 31. As such, as the actuation member 31 is rotated by exerting a pushing force thereon, as indicated by directional arrow 39', the lancet 24 is moved rearwardly and placed under tension by the biasing element 50. Eventually, however, the forward rotation of the large central gear at least partially defining the actuation member 31 will be such that the gear segment 32 will be disengaged from the track 28 on the lancet 24. The lancet 24 will thereby be released causing it to be effectively fired and move into its piercing orientation. In such an embodiment, any of a variety of different components could be utilized so as to prevent subsequent movement of the large central gear of the actuation member 31. However, a restriction assembly comprising a restrictor member or biasing element 27 and stop member or abutment element 33, as described above will provide sufficient safety to prevent re-firing of the lancet 24.

Figure 8:
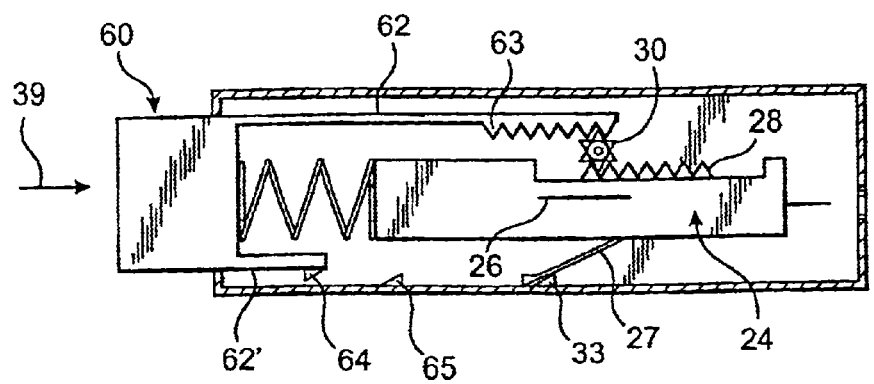
FIG. 8 is a side cross sectional view of yet another alternative embodiment of the single use lancet device of the present invention.

FIG. 8 represents yet another embodiment of the present invention, wherein the actuation assembly may be configured as a rear push button, generally indicated as 60. In this embodiment, the rear push button actuation assembly 60 includes an elongate element 62 mounted on the interior of the housing 20 and provided with a gear track 63 formed thereon. This gear track 63 is disposed and configured to movably engage and manipulate the positioning member or rotating gear 30. The gear 30 is also disposed in movably engaging relation with the gear track 28 fixedly secured to lancet 24. Forward movement of the push button actuation assembly 60 and the track 63, in accordance with directional arrow 39, causes the appropriate rearward movement of the lancet 24 due to the interconnection of the gear 30 with both the tracks 63 and 28. The lancet 24 is thereby compressed against the biasing element 50 of the driving assembly and then subsequently released causing the firing of the lancet 24.

In such an embodiment, the restriction assembly may comprise a restrictor member in the form of an abutment head 64 and a corresponding stop member in the form of an abutment element 65 associated with the elongated element 62 or with an oppositely disposed element 62', as illustrated in FIG. 8. In either such embodiment, after lancet 24 has been fired due to sufficient forward movement of the push button actuation assembly 60 into a compressed position, the push button actuation assembly 60 can not be withdrawn from its compressed position within the housing 20 and it can not be re-used.

Figure 9:
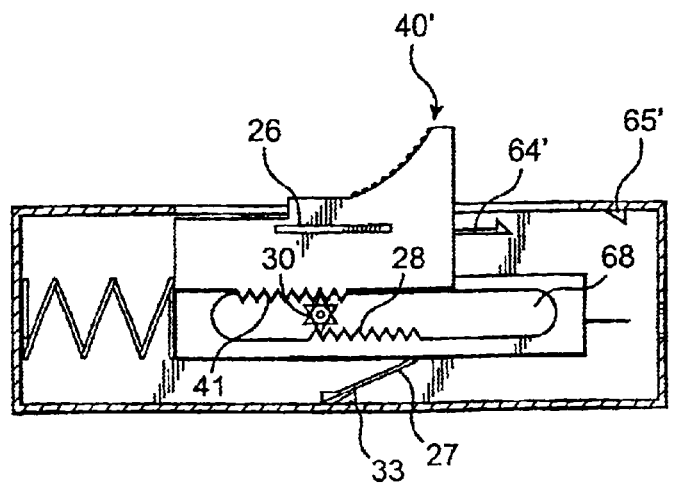
FIG. 9 is a side cross sectional view of still another embodiment of the single use lancet device of the present invention.
Figure 10:
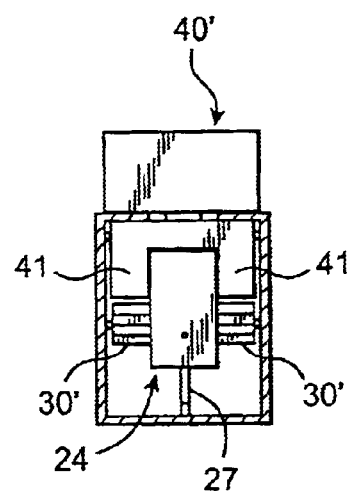
FIG. 10 is a front, interior view of the embodiment of FIG. 9.

Moreover, in the embodiment of FIGS. 9 and 10, the actuation assembly 40' may also be configured to achieve a degree of sliding stability for the lancet 24. In this embodiment, a gear 30' protrudes from either one or both sides of the lancet 24 into movable engagement with one or more downwardly depending track segments 41 secured to the actuation assembly 40'. Interconnection and moveable engagement of the gear 30' with the gear tracks 41 and 28 cause the corresponding movement of the lancet 24 rearward into a compressed position from which it is subsequently released into the fired position.

Also, in the embodiment of FIGS. 9 and 10, a slot 68 may be provided within the lancet 24 so as to effectively receive the gear 30'. Of course, an open top or bottom configuration may also be effectively achieved, so long as the gear track 28 is appropriately positioned. Indeed, if desired the gear track 28 may be configured on the same side of the gear 30' as the actuation assembly 40'. However, in such a variation of this embodiment further modification of the actuation assembly 40' may be desired.

Further included in the embodiment of FIG. 9, is a restriction assembly which may comprise, in addition to or instead of biasing element 27 and abutment 33, abutment head 64' and housing abutment 65'. The actuation assembly 40' may thereby be locked in a position by interaction of the abutment elements 64' and 65' in a manner similar to that described with reference to the embodiment of FIG. 8, after it is been used to fire the lancet 24. Accordingly, whether positioned to the forward or rear end of the actuation assembly 40, 40', it is seen that a trigger lock assembly may be provided which can effectively achieve securement of the actuation assembly 40' and prevent intended and/or accidental re-use of the single use lancet device 10 of the present invention.

In addition, at least some if not all of the embodiments of the present invention include the side track or wing 26 preferably disposed and structured to achieve stability for the lancet 24 during the movement thereof.

Since many modifications, variations and changes in detail can be made to the described preferred embodiment of the invention, it is intended that all matters in the foregoing description and shown in the accompanying drawings be interpreted as illustrative and not in a limiting sense.

What is claimed is:

1. A single use lancet device comprising:
   a) a housing,
   b) a lancet movably disposed within said housing and including a piercing tip,
   c) an actuation assembly mounted on said housing and releasably and drivingly connected to said lancet,
   d) said actuation assembly selectively movable to dispose said lancet at least into a cocked orientation,
   e) a driving assembly disposed in driving engagement with said lancet and structured to move said lancet from said cocked orientation at least temporarily into a piercing orientation, and
   f) a restriction assembly disposed and structured to restrict movement of said lancet from said piercing orientation into said cocked orientation,
   g) said restriction assembly including at least one restrictor member and at least one stop member, said one restrictor member connected to said actuation assembly and movable therewith, said stop member fixedly secured to said housing and disposed in abutting relation to said one restrictor member as said lancet moves from said piercing orientation towards said cocked orientation.

2. A lancet device as recited in claim 1 wherein said driving assembly is further structured to orient said piercing tip into a retracted orientation subsequent to said lancet being disposed in said piercing orientation.

3. A lancet device as recited in claim 2 wherein said driving assembly comprises a biasing member disposed in biasing engagement with said lancet on said lancet is in said cocked orientation.

4. A lancet device as recited in claim 3 wherein said biasing member is disposed and structured to move said lancet out of said piercing orientation and dispose said piercing tip into said retracted orientation.

5. A lancet device as recited in claim 1 wherein said driving assembly is disposed and structured to force said lancet into said piercing orientation upon release of said lancet from said actuation assembly.

6. A lancet device as recited in claim 5 wherein said driving assembly is further structured to orient said piercing tip automatically into a retracted orientation subsequent to said lancet being disposed in said piercing orientation.

7. A lancet device as recited in claim 1 further comprising a positioning assembly movably and releasably interconnecting said actuation assembly and said lancet.

8. A lancet device as recited in claim 7 wherein said positioning assembly is disposed in concurrent engagement with both said actuation assembly and said lancet as said lancet is being disposed into said cocked orientation.

9. A lancet device as recited in claim 8 wherein said driving assembly and positioning assembly are cooperatively disposed and structured to force said lancet into said piercing orientation upon release of said positioning assembly from at least one of said actuation assembly or lancet.

10. A lancet device as recited in claim 7 wherein said lancet is positioned from said cocked orientation into said piercing orientation upon disposition of said positioning assembly out of concurrent engagement with said lancet and said actuation assembly.

11. A lancet device as recited in claim 7 wherein said positioning assembly comprises at least one positioning member movably and releasably interconnecting said lancet and said actuation assembly.

12. A lancet device as recited in claim 11 wherein said positioning member is disposed in concurrent engagement with both said lancet and said actuation assembly as said lancet moves into said cocked orientation and said positioning member is disconnected from at least one of said lancet and actuation member upon moving into said piercing orientation from said cocked orientation.

13. A lancet device as recited in claim 12 wherein said positioning member is movable relative to both said lancet and said actuation assembly.

14. A lancet device as recited in claim 12 wherein said positioning member is fixedly secured to said actuation assembly and disposed in movable and detachable relation to said lancet.

15. A lancet device as recited in claim 12 wherein said positioning member comprises a gear structure.

16. A lancet device as recited in claim 7 wherein said positioning assembly is movable relative to both said lancet and said actuation assembly.

17. A lancet device as recited in claim 7 wherein said positioning assembly is fixedly secured to said actuation assembly and disposed in movable and detachable relation to said lancet.

18. A lancet device as recited in claim 7 wherein said positioning assembly comprises a gear structure.

19. A lancet device as recited in claim 1 wherein said one restrictor member is secured to said lancet and movable therewith.

20. A lancet device as recited in claim 1 wherein said restriction assembly comprises a first restrictor member and a first stop member and a second restrictor member and a second stop member, said first and second restrictor members each connected to a different one of said lancet or actuation assembly and movable therewith, said first and second stop members fixedly secured to said housing and disposed in abutting relation to a corresponding one of said first or second restrictor members as said lancet moves from said piercing orientation towards said cocked orientation.

21. A single use lancet device comprising:
   a) a housing,
   b) a lancet movably disposed within said housing and including a piercing tip,
   c) an actuation assembly movably mounted on said housing in driving relation to said lancet,
   d) a positioning assembly movably and releasably interconnecting said actuation assembly and said lancet, e) said actuation assembly selectively positionable to dispose said lancet at least into a cocked orientation, f) a driving assembly disposed in biasing relation to said lancet and structured to position said lancet at least temporarily into a piercing orientation, and g) said driving assembly and said positioning assembly cooperatively disposed and structured to force said lancet into said piercing orientation upon release of said positioning assembly from at least one of said actuation assembly or said lancet, and h) said positioning assembly including at least one positioning member movably and releasably interconnecting said lancet and said actuation assembly, and disposed in concurrent engagement with both said lancet and said actuation assembly as said lancet moves into said cocked orientation and said positioning member is disconnected from at least one of said lancet and said actuation assembly upon moving into said piercing orientation from said cocked orientation.

22. A lancet device as recited in claim 21 wherein said driving assembly is disposed and structured to move said lancet out of said piercing orientation and dispose said piercing tip into said retracted orientation.

23. A lancet device as recited in claim 21 further comprising a restriction assembly disposed and structured to restrict movement of said lancet from said piercing orientation into said cocked orientation.

24. A lancet device as recited in claim 23 wherein said restriction assembly comprises at least one restrictor member and at least one stop member, said one restrictor member connected to one of said lancet or said actuation assembly and movable therewith, and said stop member fixedly secured to said housing and disposed in abutting relation to said one restrictor member as said lancet moves from said piercing orientation towards said cocked orientation.

25. A single use lancet assembly comprising:

a) a housing, b) a lancet movably disposed within said housing and including a piercing tip, c) an actuation assembly movably disposed in driving engagement with said lancet, d) at least two engagement elements disposed to operatively interconnect said actuation assembly and said lancet at least upon engagement therebetween, e) said actuation assembly structured to position said lancet at least temporarily into a cocked orientation upon actuation thereof concurrent with said engagement between said engagement elements, f) a driving assembly drivingly engaging said lancet, g) said actuation assembly further structured to effect dis-engagement between said engagement elements upon continued actuation thereof after said lancet is disposed in said cocked orientation, and h) said driving assembly structured to move said lancet at least temporarily into a piercing orientation upon said disengagement between said engagement elements.

* * * * *